US011286453B2

(12) United States Patent
Lin et al.

(10) Patent No.: US 11,286,453 B2
(45) Date of Patent: Mar. 29, 2022

(54) CONTINUOUS MICROALGAE CULTURE MODULE AND METHOD OF CULTURING MICROALGAE CONTAINING MACULAR PIGMENT

(71) Applicant: National Chiao Tung University, Hsinchu (TW)

(72) Inventors: Chih-Sheng Lin, Hsinchu (TW); Chiu-Mei Kuo, Hsinchu (TW); Yi-Chun Yang, Taichung (TW); Wen-Xin Zhang, Kaohsiung (TW)

(73) Assignee: National Chiao Tung University, Hsinchu (TW)

( * ) Notice: Subject to any disclaimer, the term of this patent is extended or adjusted under 35 U.S.C. 154(b) by 346 days.

(21) Appl. No.: 16/202,921

(22) Filed: Nov. 28, 2018

(65) Prior Publication Data
US 2019/0382704 A1 Dec. 19, 2019

(30) Foreign Application Priority Data
Jun. 13, 2018 (TW) ................................ 107120404

(51) Int. Cl.
*C12M 3/00* (2006.01)
*C12N 1/12* (2006.01)
*C12M 1/00* (2006.01)

(52) U.S. Cl.
CPC ............ *C12M 23/44* (2013.01); *C12M 21/02* (2013.01); *C12M 23/58* (2013.01); *C12N 1/12* (2013.01)

(58) Field of Classification Search
CPC ...... C12M 23/44; C12M 23/58; C12M 21/02; C12N 1/12

USPC ....................................................... 435/294.1
See application file for complete search history.

(56) References Cited

U.S. PATENT DOCUMENTS

| 6,805,800 | B1 | 10/2004 | Keating | |
|---|---|---|---|---|
| 7,997,025 | B1* | 8/2011 | Masse | C12M 41/06 47/1.4 |
| 8,241,895 | B2* | 8/2012 | Hu | C12M 23/44 435/292.1 |

(Continued)

FOREIGN PATENT DOCUMENTS

| CN | 106399111 A | 2/2017 |
|---|---|---|
| TW | 201333187 A | 8/2013 |
| WO | 2012065545 A1 | 5/2012 |

OTHER PUBLICATIONS

Anderson, G. A., The Society for engineering in agricultural, food, and biological systems (Jul. 2003), Study of Light as a parameter in the growth of algae in a Photo-Bioreactor (PBR) (Year: 2003).*

(Continued)

*Primary Examiner* — Michael L Hobbs
*Assistant Examiner* — Lenora A Abel
(74) *Attorney, Agent, or Firm* — Servilla Whitney LLC (57) ABSTRACT

Provided is a continuous microalgae culture module, including an outdoor culture unit, a high-density culture unit, a pigment induced unit, and a harvesting unit. A method of culturing microalgae containing macular pigment is also provided, including sequentially culturing microalgae with medium in the outdoor culture unit and the high-density culture unit, producing macular pigment in the pigment induced unit through different light irradiation, and collecting the microalgal biomass containing macular pigment in the harvesting unit.

19 Claims, 7 Drawing Sheets

(56) References Cited

U.S. PATENT DOCUMENTS

| | | | |
|---|---|---|---|
| 2009/0035835 A1 | 2/2009 | Slavin | |
| 2010/0218674 A1* | 9/2010 | Fujikawa | B01D 53/1425 |
| | | | 95/42 |
| 2011/0070632 A1* | 3/2011 | Katoch | B08B 1/008 |
| | | | 435/286.6 |
| 2014/0242681 A1* | 8/2014 | Fiorentino | C12N 1/12 |
| | | | 435/287.1 |
| 2015/0004685 A1* | 1/2015 | Carl | B01D 53/84 |
| | | | 435/292.1 |

OTHER PUBLICATIONS

Chen et al., Journal of Nanomaterials, vol. 2014, Article ID 217537, 9 pages, 2014. https://doi.org/10.1155/2014/217537, Chitosan and Its Derivatives Applied in Harvesting Microalgae for Biodiesel Production: An Outlook (Year: 2014).*

Goldman et al., Journal of Experimental marine Biology and Ecology, vol. 57, Issue 1, Jan. 8, 1982, pp. 1-13, The effect of pH in intensive microalgal cultures. I. Biomass regulation (Year: 1982).*

Baek, Kwangryul, et al., "Photoautotrophic production of macular pigment in a Chlamydomonas reinhardtii strain generated by using DNA-free CRISPR-Cas9 RNP-mediated mutagenesis", Biotechnology and Bioengineering, 2018 115:719-728.

Chiu, Pai-Ho, et al., "Cultivation of two thermotolerant microalgae under tropical conditions: Influences of carbon sources and light duration on biomass and lutein productivity in four seasons", Bioresource Technology, 2016, 30 pages.

Gong, Mengyue, et al., "Investigation of Chlorella vulgaris UTEX 265 cultivation under light and low temperature stressed conditions for lutein production in flasks and the coiled tree photo-bioreactor (CTPBR)", Appl. Biochem. Biotechnol., Jun. 24, 2017, 20 pages.

Jeon, Jin Young, "Optimization of Culture Media for Large-Scale Lutein Production by Heterotrophic Chlorella vulgaris", American Institute of Chemical Engineers, Biotechnol. Prog., vol. 30, No. 3, 2014.

* cited by examiner

CONTINUOUS MICROALGAE CULTURE MODULE AND METHOD OF CULTURING MICROALGAE CONTAINING MACULAR PIGMENT

CROSS-REFERENCE TO RELATED APPLICATION

This application claims priority to Taiwan Application Serial Number 107120404, filed Jun. 13, 2018, which is herein incorporated by reference in its entirety.

BACKGROUND

Field of Invention

The present invention relates to a microalgae culture module and method of culturing microalgae. More particularly, the present invention relates to a continuous microalgae culture module and method of culturing microalgae containing macular pigment.

Description of Related Art

The main pigments in the macular region of the retina are lutein and zeaxanthin. Therefore, lutein and zeaxanthin are also referred to as macular pigment for use in improving eyesight, protecting retina, reducing cataract, and preventing macular degeneration. Most of the macular pigment in the commercial product is obtained from the calendula flowers. However, the cultivation of calendula flowers is limited recently due to the climate change and the limitation of the cultivated land, microalgae becomes one of other resources to obtain the macular pigment. The advantage of macular pigment obtained from microalgae is that microalgae can be cultured on non-cultivated land, does not require large amounts of cultivated land, and can harvest throughout the year without seasonal limitation.

Currently, there are two ways for the large-scale microalgae cultivation, open ponds and closed photobioreactors. The cost of the open ponds included raceway pond and circular pond are lower than the closed photobioreactors. However, the biggest problem of the open ponds is that it cannot effectively control environmental factors, such as low cell density of algae after cultivating, easy contamination by other microalgae, large water requirement, and large evaporation rate. The closed photobioreactors can achieve high cell density and high yields of microalgae after cultivating, hard contamination by other microalgae, less water requirement, and less water evaporation rate. However, light efficiency, gas exchange efficiency, and stirring efficiency of the closed photobioreactors will directly affect the biomass productivity of microalgae.

Furthermore, the culture conditions for growing microalgae and for producing bio-functional substances from microalgae are not necessarily the same. The prior arts mostly focus on large production of microalgae in order to obtain sufficient microalgal bio-functional substances. Therefore, a device for simultaneously producing a large amount of microalgae and a large amount of microalgal bio-functional substances is needed, and the disadvantage of the prior art should be resolved.

SUMMARY

The invention provides a continuous microalgae culture module, comprising an outdoor culture unit, a high-density culture unit, a pigment inducing unit, and a harvesting unit. The continuous microalgae culture module can continuously produce the microalgae (microalgal biomass) and induce the microalgae to produce a large amount of the macular pigment, so that the continuous microalgae culture module has industrial applicability.

The invention provides a continuous microalgae culture module, comprising an outdoor culture unit, a high-density culture unit, a pigment inducing unit, and a harvesting unit. The outdoor culture unit configures to contain microalgae and a medium, the microalgae produces macular pigment. The high-density culture unit is connected to the outdoor culture unit by pipeline, and the high-density culture unit comprises a first light source. The pigment inducing unit comprises a culture device and a second light source. The culture device comprises a first inlet and a first outlet, and the first inlet is connected to the high-density culture unit. The second light source is adjacent to the culture device, and the second light source is capable of emitting a blue light. The harvesting unit comprises a collecting tank comprising a second inlet and a second outlet. The second inlet is located at an upper portion of the collecting tank and is connected to the first outlet of the culture device of the pigment inducing unit. The second outlet is located at a lower portion of the collecting tank.

In one embodiment, the outdoor culture unit comprises a plurality of first containers. The first containers are connected in a manner such that the media and the microalgae pass through the first containers in a series or parallel manner. The first containers can be connected in series or in parallel so that the production of microalgae culture can be adjusted.

In one embodiment, the first containers are transparent columns.

In one embodiment, the first light source of the high-density culture unit is capable of emitting red light.

In one embodiment, the high-density culture unit further comprises a plurality of second containers. Adjacent ones of the second containers are connected with each other, and the first light source is adjacent to the second containers.

In one embodiment, the second containers are connected in a manner such that the media and the microalgae pass through the second containers in a series or parallel manner. The second containers can be controlled in series or in parallel connection so that the scale of microalgae culture can be adjusted.

In one embodiment, the second containers are transparent columns.

In one embodiment, the culture device of the pigment inducing unit is a flexible transparent hose surrounding the second light source.

In one embodiment, the harvesting unit further comprises at least one branch pipe and a stirring device. The at least one branch pipe is located above the second outlet and at one side of the collecting tank. The at least one branch pipe is connected to the outdoor culture unit. The stirring device is located inside the collecting tank.

In one embodiment, the continuous microalgae culture module further comprises a gas supplying unit and a gas recovery unit. The gas supplying unit comprises a gas delivery device, a first pump, and a second pump. The first pump is connected to the gas delivery device and the bottom of the outdoor culture unit. The second pump is connected to the gas delivery device and the bottom of the high-density culture unit. The gas recovery unit comprises a gas collecting device and a gas controlling device. The gas collecting device is connected to a top of the outdoor culture unit and a top of the high-density culture unit. The gas controlling device is connected with the first pump, the second pump of the gas supplying unit and the gas collecting device.

The invention also provides a method of culturing microalgae containing macular pigment comprises steps as follow. A medium containing microalgae in an outdoor culture unit is disposed, and the medium containing the microalgae is lighted and cultured at outdoors, such that the microalgae grow to a first density. After culturing the medium containing the microalgae at outdoors, the medium containing the microalgae is transported to a high-density culture unit, and the medium containing the microalgae is continuously lighted and cultured such that the microalgae grow to a second density larger than the first density. After culturing the medium containing the microalgae in the high-density culture unit, the medium containing the microalgae is transported to a pigment inducing unit, and the medium containing the microalgae is continuously cultured and lighted in the pigment inducing unit with the blue light, thereby increasing an amount of macular pigment in the microalgae. After culturing the medium containing the microalgae in the pigment inducing unit, the medium containing the microalgae is transported to a harvesting unit, and microalgae containing the macular pigment were collected from a bottom of a collection tank.

In one embodiment, the medium containing the microalgae is an alkaline medium.

In one embodiment, the microalgae comprise *Chlorella, Nannochloropsis, Dunaliella, Scenedesmus, Chlamydomonas, Spirulina, Botryococcus*, or combination thereof.

In one embodiment, the step of continuously lighting and culturing the medium containing the microalgae in the high-density culture unit comprises continuously illuminating the medium containing the microalgae in the high-density culture unit using a white light or red light.

In one embodiment, a wavelength of the red light ranges from 600 nm to 700 nm.

In one embodiment, in the step of culturing and continuously lighting the medium containing the microalgae in the pigment inducing unit with the blue light, the blue light has a wavelength ranged from 400 nm to 500 nm.

In one embodiment, carbon dioxide is introduced into the medium containing the microalgae in the outdoor culture unit and in the high-density culture unit simultaneously.

In one embodiment, the step of collecting the microalgae containing the macular pigment from the bottom of the harvesting unit comprises adding a flocculant into and stirring the medium containing the microalgae.

In one embodiment, the flocculant comprises an inorganic flocculant, an organic flocculant, a microbial flocculant, or a combination thereof.

In one embodiment, the flocculant comprises the organic flocculant, and the organic flocculant is chitosan.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

The following discloses several embodiments of the present disclosure. For clarity, many practical details will be illustrated in the following description. However, it should be understood that these practical details should not be limiting. In other words, in some embodiments of the present disclosure, the practical details are not essential. In addition, in order to simplify the figures, some conventionally known structures and elements are schematically illustrated in the figures.

Further, spatially relative terms, such as "beneath", "over", "upper", "lower" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

In some embodiments, the present disclosure provides a continuous microalgae culture module, which can adjust the culture conditions according to different microalgae species, to produce a large amount of and high-density of microalgae and bio-functional substances. Furthermore, the module disclosed herein can be used in carbon fixation when culturing microalgae, and $CO_2$ produced from the biogas or various industrial exhaust can be absorbed and reduced by culturing a large amount of and high-density of microalgae.

In some embodiments, the present disclosure of the continuous microalgae culture module is use for culturing the microalgae, and the industrial value of culturing the microalgae is to produce microalgae biomass and macular pigment. The microalgae can be used as biomass energy, aquatic bait, feed additive, food and nutritional supplement. The macular pigment can be used as a natural carotenoid raw material, and the macular pigment also can be applied to foods, feed additives, skin care products, and nutritional supplements.

Figure 1:
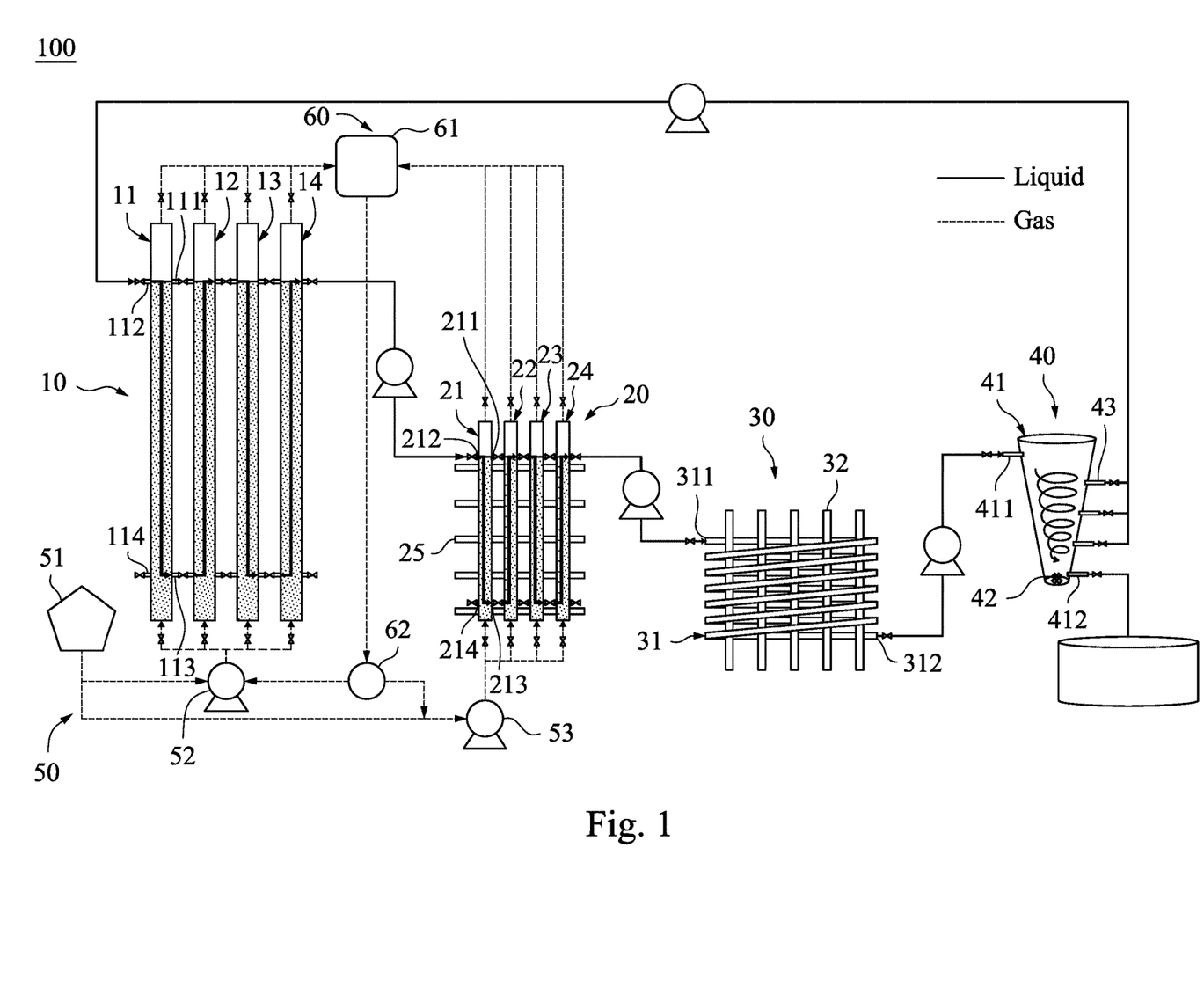
FIG. 1 is a schematic diagram illustrating a continuous microalgae culture module in which all the first containers and the second containers are connected in series according to one embodiment of the present disclosure.

FIG. 1 is a schematic diagram illustrating a continuous microalgae culture module 100 according to one embodiment of the present disclosure. The continuous microalgae culture module 100 comprises an outdoor culture unit 10, a high-density culture unit 20, a pigment inducing unit 30, a harvesting unit 40, a gas supplying unit 50, and a gas recovery unit 60.

The outdoor culture unit 10 comprises a plurality of first containers, such as a first container 11, a first container 12, a first container 13, and a first container 14. The first containers 11, 12, 13, 14 serve the function of containing a medium and microalgae for producing macular pigment, and the first containers 11, 12, 13, 14 are connected with each other. Each of the first containers 11, 12, 13, 14 comprises a first upper pipe 111, a second upper pipe 112, a first lower pipe 113, and a second lower pipe 114. Each first upper pipe 111 is located at the upper portion of a corresponding one of the first containers 11, 12, 13, 14. Each second upper pipe 112 is arranged at a position opposite to the first upper pipe 111 and located at the upper portion of one of the first containers 11, 12, 13, 14. In other words, as shown in FIG. 1, the pipe located at the right side of the upper portion of each of the first containers 11, 12, 13, 14 is called the first upper pipe 111, and the pipe located at the left side of the upper portion of each of the first containers 11, 12, 13, 14 is called the second upper pipe 112. In addition, each first lower pipe 113 is located at the lower portion of each of the first containers 11, 12, 13, 14. The second lower pipe 114 is arranged at a position opposite to the first lower pipe 113 and located at the lower portion of each of the first containers 11, 12, 13, 14. In other words, as shown in FIG. 1, the pipe located at the right side of the lower portion of each of the first containers 11, 12, 13, 14 is called the first lower pipe 113, and the pipe located at the left side of the lower portion of each of the first containers 11, 12, 13, 14 is called the second lower pipe 114. In one example, the first containers 11, 12, 13, 14 are columns that are transparent to light (hereinafter referred to as "transparent columns"). The angle between the longitudinal axis of each of the transparent columns and the horizontal plane may range from 0 to 90 degree(s), and the angle can be adjusted to obtain the maximum lighting area, according to different regions, times and seasons. In one example, each of the first containers 11, 12, 13, 14 has an aeration device located at the bottom thereof.

In some embodiments, each of the first upper pipe 111, the second upper pipe 112, the first lower pipe 113, and the second lower pipe 114 has a control valve for controlling the liquid flowing there through. For example, the microalgae and the medium flow from the second upper pipe 112 of the first container 11 to the second lower pipe 114 of the first container 12 through the first lower pipe 113. Then, the microalgae and the medium flow from the first upper pipe 111 of the first container 12 to the second upper pipe 112 of the first container 13, and then the microalgae and the medium flow from the first lower pipe 113 of the first container 13 to the second lower pipe 114 of the first container 14. Finally, the microalgae and the medium flow out from the first upper pipe 111 of the first container 14. In other words, the microalgae and the medium flow downward in the first container 11 and flow upward in the first container 12, and then the microalgae and the medium flow downward in the first container 13 and flow upward in the first container 14, such that the first containers 11, 12, 13, 14 are connected in series.

In some embodiments, the first containers 11, 12, 13, 14 are transparent columns, and the volume of each of the transparent columns is 10 liters (L) to 200 L. In some examples, the volume of each of the first containers 11, 12, 13, 14 (such as transparent columns) is 10 L, 20 L, 30 L, 40 L, 50 L, 60 L, 70 L, 80 L, 90 L, 100 L, 110 L, 120 L, 130 L, 140 L, 150 L, 160 L, 170 L, 180 L, 190 L, or 200 L.

In some embodiments, the first containers 11, 12, 13, 14 are transparent columns, and the material of each of the transparent columns is plastic or glass. The plastic material includes, but not limited to, polymethyl methacrylate (PMMA), polyethylene terephthalate (PET), or polyethylene (PE).

The high-density culture unit 20 comprises a plurality of second containers, such as a second container 21, a second container 22, a second container 23, and a second container 24. Each of the second container 21, 22, 23, 24 comprises a third upper pipe 211, a fourth upper pipe 212, a third lower pipe 213, and a fourth lower pipe 214. Each third upper pipe 211 is located at an upper portion of a corresponding one of the second containers 21, 22, 23, 24, and the fourth upper pipe 212 is arranged at a position opposite to the third upper pipe 211 and located at the upper portion of each of the second containers 21, 22, 23, 24. Each third lower pipe 213 is located at a lower portion of a corresponding one of the second containers 21, 22, 23, 24. The fourth lower pipe 214 is arranged at a position opposite to the third lower pipe 213 and located at the lower portion of each of the second containers 21, 22, 23, 24. In one example, the second containers 21, 22, 23, 24 are transparent columns for increasing the light penetration when culturing the microalgae. In one example, each of the second containers 21, 22, 23, 24 has an aeration device located at the bottom thereof so that the incoming gas can equally and sufficiently be dissolved in the medium.

In some embodiments, each of the third upper pipe 211, the fourth upper pipe 212, the third lower pipe 213, and the fourth lower pipe 214 has a control valve for controlling the liquid flowing there through. For example, the microalgae and the medium flow from the first upper pipe 111 of the first container 14 to the fourth upper pipe 212 of the second container 21, and then the microalgae and the medium flow from the third lower pipe 213 of the second container 21 to the fourth pipe 214 of the second container 22. Then, the microalgae and the medium flow from the third upper pipe 211 of the second container 22 to the fourth upper pipe 212 of the second container 23, and then the microalgae and the medium flow from the third lower pipe 213 of the second container 23 to the fourth lower pipe 214 of the second container 24. Finally, the microalgae and the medium flow out from the third upper pipe 211 of the second container 24. In other words, the microalgae and the medium flow downward in the second container 21 and flow upward in the second container 22, and then the microalgae and the medium flow downward in the second container 23 and flow upward in the second container 24, such that the second containers 21, 22, 23, 24 are connected in series. The first upper pipe 111 of the first container 14 is connected to the fourth upper pipe 212 of the second container 21 through a pump, so that the microalgae and the medium can be transported from the first containers 11, 12, 13, 14 to the second containers 21, 22, 23, 24.

In some embodiments, the second containers 21, 22, 23, 24 of the high-density culture unit 20 are transparent columns, and the volume of each of the transparent columns is 10 liters (L) to 100 L. In some examples, the volume of each of the second containers 21, 22, 23, 24 (such as transparent columns) is 10 L, 20 L, 30 L, 40 L, 50 L, 60 L, 70 L, 80 L, 90 L, or 100 L.

In some embodiments, the second containers 21, 22, 23, 24 are transparent columns, and the material of each of the transparent columns is plastic or glass. The plastic material includes, but not limited to, PMMA, PET, or PE.

In some embodiments, the high-density culture unit 20 further comprises a first light source 25 adjacent to the second containers 21, 22, 23, 24. In some examples, the first light source 25 is capable of emitting red light. In some examples, the wavelength of the red light ranges from 600 nm to 700 nm, so that the microalgae can rapidly grow to achieve high-yield microalgae biomass. In some examples, the wavelength range of the red light is 600 nm, 610 nm, 620 nm, 630 nm, 640 nm, 650 nm, 660 nm, 670 nm, 680 nm, 690 nm, or 700 nm.

The pigment inducing unit 30 comprises a culture device 31 and a second light source 32. The culture device 31 comprises a first inlet 311 and a first outlet 312, and the first inlet 311 may be connected to any one of the second containers 21, 22, 23, 24, depending on the number of the second containers 21, 22, 23, 24 and the need. In some examples, the first inlet 311 of the culture device 31 is connected to the third upper pipe 211 of the second container 24 of the high-density culture unit 20. In some examples, the third upper pipe 211 of the second container 24 is connected to the first inlet 311 of the culture device 31 through a pump, so that the microalgae and the medium can be transported from the second containers 21, 22, 23, 24 to the culture device 31. In some examples, the culture device 31 is a flexible transparent hose surrounding the second light source 32. In some examples, the material of the flexible transparent hose includes, but not limited to, polyvinyl chloride (PVC), polyurethane (PU), polyethylene (PE), polypropylene (PP), polyamide (PA), or fluorinated ethylene propylene (FEP). The pigment inducing unit 30 is configured for producing macular pigment in the microalgae. In some examples, a number of lightening ways may be used to induce the microalgae to produce macular pigment. In examples, the flexible transparent hose may surround the second light source 32, or the second light source 32 may surround the flexible transparent hose, or the second light source 32 may be inserted into the flexible transparent hose, or a combination thereof. The second light source 32 is adjacent to the culture device 31, and the second light source 32 is capable of emitting blue light. In some examples, a wavelength of the blue light ranges from 400 nm to 500 nm, so that the macular pigment can be rapidly induced in the microalgae and the production of the macular pigment can be enhanced. In some examples, the wavelength range of the blue light is 400 nm, 410 nm, 420 nm, 430 nm, 440 nm, 450 nm, 460 nm, 470 nm, 480 nm, 490 nm, or 500 nm.

The harvesting unit 40 comprises a collecting tank 41, a stirring device 42, and at least one branch pipe 43. The collecting tank 41 comprises a second inlet 411 and a second outlet 412. The second inlet 411 is located at the upper portion of the collecting tank 41 and connected to the first outlet 312 of the culture device 31 of the pigment inducing unit 30. The first outlet 312 is connected to the second inlet 411 through a pump, so that the microalgae and the medium can be transported from the culture device 31 to the collecting tank 41. The second outlet 412 is located at the bottom of the collecting tank 41. In some example, the collecting tank 41 is formed in cylindrical or conical shape. The stirring device 42 is located inside the collecting tank 41, and may include a stirring paddle or stirring rod, for example. The at least one branch pipe 43 is located above the second outlet 412 and at a side of the collecting tank 41. The at least one branch pipe 43 is connected to the second upper pipe 112 (or second lower pipe 114) of the first container 11 of the outdoor culture unit 10. In some examples, the at least one branch pipe 43 includes three branch pipes 43 which are sequentially arranged from the upper portion to the lower portion of the collecting tank 41, and each of the branch pipes 43 has a control valve for controlling the medium outflow.

The gas supplying unit 50 comprises a gas delivery device 51, a first pump 52, and a second pump 53. The first pump 52 is connected to the gas delivery device 51, and is further connected to the bottom of each of the first containers 11, 12, 13, 14. The second pump 53 is connected to the gas delivery device 51, and is further connected to the bottom of each of the second containers 21, 22, 23, 24.

The gas recovery unit 60 comprises a gas collecting device 61 and a gas controlling device 62. The gas collecting device 61 is connected to the top of each of the first containers 11, 12, 13, 14 of the outdoor culture unit 10. The gas collecting device 61 is also connected to the top of each of the second containers 21, 22, 23, 24 of the high-density culture unit 20 by a pipeline. The gas controlling device 62 is connected with the first pump 52 and the second pump 53 of the gas supplying unit 50, and the gas collecting device 61. In some examples, the gas may be continuously introduced into the outdoor culture unit 10 and the high-density culture unit 20 from the same gas source. In some examples, the gases introduced into the outdoor culture unit 10 and the high-density culture unit 20 are supplied from the same gas source but mixed with air in different ratios. In some examples, the gas introduced into the outdoor culture unit 10 and the high-density culture unit 20 is supplied from different gas sources in different ratios.

Figure 2:
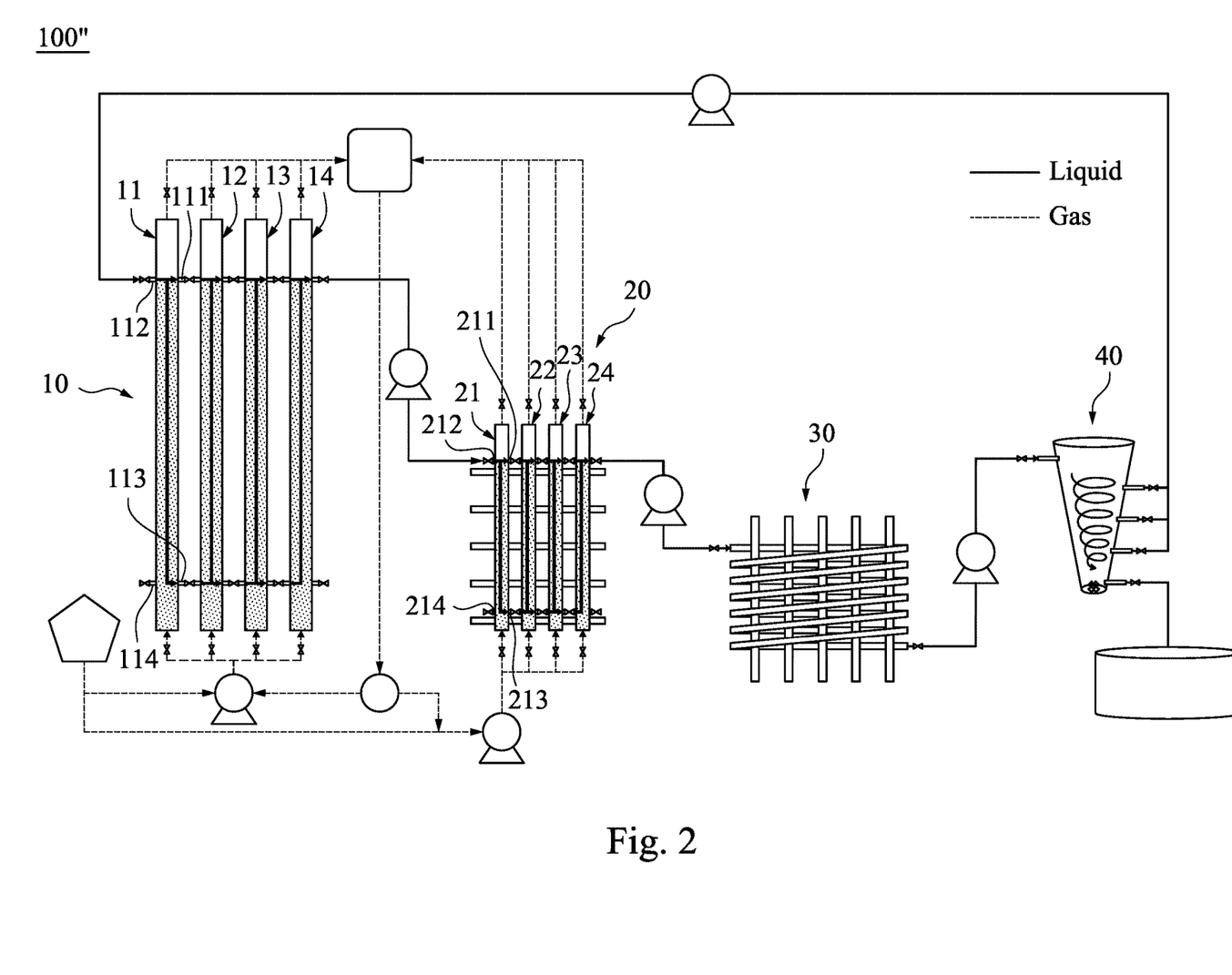
FIG. 2 is a schematic diagram illustrating a continuous microalgae culture module in which all the first containers and the second containers are connected in parallel connection according to another embodiment of the present disclosure.

FIG. 2 is a schematic diagram of the continuous microalgae culture module 100" according to another embodiment of the present disclosure. The differences between FIG. 1 and FIG. 2 are in that the upper pipes of two adjacent ones of the first containers 11, 12, 13, 14 are connected with each other, and the lower pipes of two adjacent ones of the first containers 11, 12, 13, 14 are connected with each other. Therefore, the first containers 11, 12, 13, 14 are connected to each other in parallel. Specifically, the first upper pipe 111 of the first container 11 is connected to the second upper pipe 112 of the first container 12, and the first lower pipe 113 of the first container 11 is connected to the second lower pipe 114 of the first container 12. The first upper pipe 111 of the first container 12 is connected to the second upper pipe 112 of the first container 13, and the first lower pipe 113 of the first container 12 is connected to the second lower pipe 114 of the first container 13. The first upper pipe 111 of the first container 13 is connected to the second upper pipe 112 of the first container 14, and the first lower pipe 113 of the first container 13 is connected to the second lower pipe 114 of the first container 14.

Furthermore, in the high-density culture unit 20, the upper pipe of two adjacent ones of the second containers 21, 22, 23, 24 are connected with each other, and the lower pipes of two adjacent ones of the second containers 21, 22, 23, 24 are connected with each other. Therefore, the second containers 21, 22, 23, 24 are connected to each other in parallel. Specifically, the third upper pipe 211 of the second container 21 is connected to the fourth upper pipe 212 of the second container 22, and the third lower pipe 213 of the second container 21 is connected to the fourth lower pipe 214 of the second container 22. The third upper pipe 211 of the second container 22 is connected to the fourth upper pipe 212 of the second container 23, and the third lower pipe 213 of the second container 22 is connected to the fourth lower pipe 214 of the second container 23. The third upper pipe 211 of the second container 23 is connected to the fourth upper pipe 212 of the second container 24, and the third lower pipe 213 of the second container 23 is connected to the fourth lower pipe 214 of the second container 24.

The present disclosure also provides a method of culturing microalgae containing macular pigment.

Although a series of operations or steps are used below to describe the method disclosed herein, an order of these operations or steps should not be construed as a limitation to the present invention. For example, some operations or steps may be performed in a different order and/or other steps may be performed at the same time. In addition, all shown operations, steps and/or features are not required to be executed to implement an embodiment of the present invention. In addition, each operation or step described herein may include a plurality of sub-steps or actions.

The method of culturing microalgae containing macular pigment of the present disclosure comprises the steps described below. A medium containing the microalgae is disposed in an outdoor culture unit, and is lighted and cultured at outdoors such that the microalgae grow to a first density. Then, the medium containing the microalgae is transported to a high-density culture unit, and the medium containing the microalgae is continuously lighted and cultured such that the microalgae grow to a second density greater than the first density. And then, the medium containing the microalgae is transported to a pigment inducing unit, and the medium containing the microalgae is cultured and continuously lighted with the blue light, thereby increasing an amount of macular pigment in the microalgae. Thereafter, the medium containing the microalgae is transported to a harvesting unit, and microalgae containing macular pigment are collected from at a bottom of a collection tank after stirring.

EXAMPLES

Figure 3:
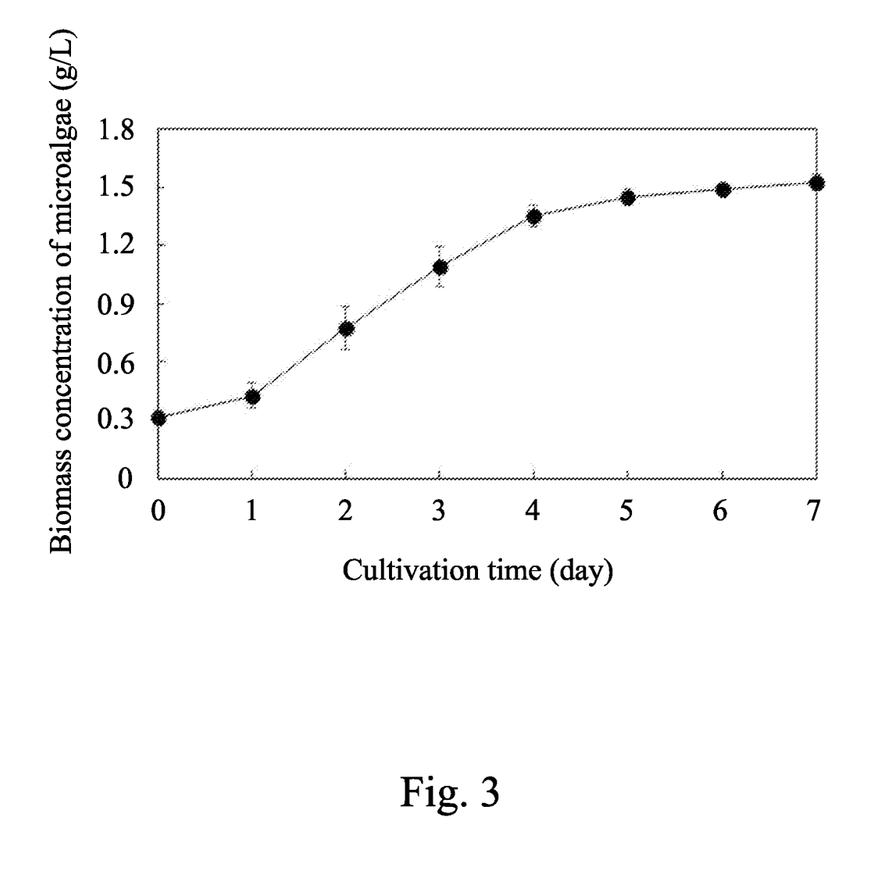
FIG. 3 is a line chart showing the biomass concentration of microalgae cultured in the outdoor culture units according to one embodiment of the present disclosure.

As shown in FIG. 1, the first containers 11, 12, 13, and 14 of the outdoor culture unit 10 are four transparent columns each having a volume of 60 L (16 cm in diameter, 300 cm in high). The total culture volume is 240 L, and two adjacent first containers 11, 12, 13, 14 are connected in series. During the experiments, 90% of the weather was sunny day, and the rest was cloudy day. The average sunshine duration was 11.3 hours. The light intensity of sunny day was greater than 1,000 μmol/m$^2$/s. The average daily temperature was 28° C., and the averaged night temperature was 26° C. The rate of gas flow was 0.2 vvm (0.2 liters of gas passing through per liter of liquid per minute). The initial biomass concentration of microalgae in the medium was 0.3 g/L of *Chlorella vulgaris*, and the composition of the medium comprised of 1.25 g $KNO_3$, 1.25 g $KH_2PO_4$, 1 g $MgSO_4.7H_2O$, 83.5 mg $CaCl_2.2H_2O$, 0.1142 g $H_3BO_3$, 49.8 mg $FeSO_4.7H_2O$, 88.2 mg $ZnSO_4.7H_2O$, 14.4 mg $MnCl_2.4H_2O$, 10 mg $CuSO_4$, 7.1 mg $Na_2MoO_4$, and 4 mg $CoCl_2.6H_2O$ per liter. From 6 a.m. to 6 p.m., 2 vol % $CO_2$ was introduced into the first containers 11, 12, 13, 14 through the first pump 52 by the gas delivery device 51 of the gas supplying unit 50, and air was introduced into the first containers 11, 12, 13, 14 at the rest of the time. The medium containing the microalgae with initial biomass concentration of 0.3 g/L was continuously introduced into the first container 11. The medium containing the microalgae flowed sequentially through the first container 12, the first container 13, and the first container 14 with the increase of cultivation time. The average retention time was 7 days. At day 7, the biomass concentration of the microalgae flowed from the first upper pipe 111 of the first container 14 was approximately 1.5 g/L, and the productivity of the microalgae was 0.171 g/L/day as shown in FIG. 3.

Figure 4:
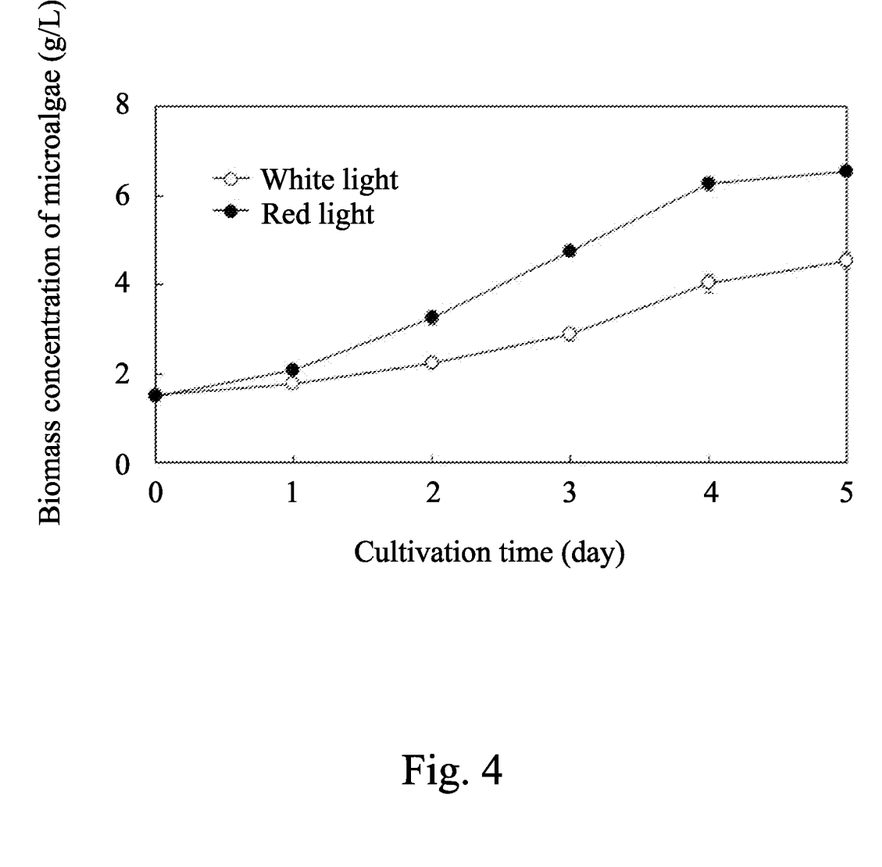
FIG. 4 is a line chart showing the biomass concentration of microalgae cultured in high-density culture unit illuminated by white light or red light according to some embodiments of the present disclosure.

The high-density culture unit 20 comprises a number of second containers comprised of twenty-four 10 L transparent columns (FIG. 1 only illustrates four second containers 21, 22, 23, 24 as an example). The second containers are connected in series. After the medium containing the microalgae was cultured by the outdoor culture unit 10, there is a biomass concentration of *Chlorella* 1.5 g/L in the medium, and the medium flows to the high-density culture unit 20 at a flow rate of 35 L/day. 2 vol % $CO_2$ was introduced into the second containers 21, 22, 23, 24 by the gas delivery device 51 of the gas supplying unit 50 through the second pump 53. The flow rate of 2 vol % $CO_2$ was 0.2 vvm and the temperature was 26° C. The medium containing the microalgae flowed sequentially through twenty-four 10 L transparent columns. In one example, the microalgae in outdoor culture unit 10 and high-density culture unit 20 was cultured in an alkaline medium, thereby increasing the solubility of $CO_2$ and enhancing the growth of microalgae. The alkaline medium comprised of, but not limited to, inorganic alkaline such as sodium hydroxide (NaOH), sodium bicarbonate ($NaHCO_3$), and potassium hydroxide (KOH), and the pH of the alkaline medium was controlled by intermittently introducing $CO_2$ to the high-density culture unit 20. The experiment was divided into two groups for comparing the growth rate of microalgae in both groups. In group (1), the microalgae was continuously illuminated by the first light source 25 which is capable of emitting red light from red LED tubes (with light intensity of 300 μmol/m$^2$/s); and in group (2) the microalgae was continuously illuminated by the first light source 25 which is capable of emitting white light from white LED tubes (with light intensity of 300 μmol/m$^2$/s). As shown in FIG. 4, after the medium containing the microalgae was continuously cultured in the high-density culture unit 20 in an average retention time of 5 days (i.e., day 12), the biomass concentrations of the microalgae flowing out of the high-density culture unit 20 were 6.5 g/L in the red light group and 4.5 g/L in the white light group. The growth rate of *Chlorella* cultured with red light illumination was better than that cultured with white light illumination. The productivity of the microalgae with the continuous illumination of red light after 5 days (i.e., day 12) was 1.009 g/L/day, which was 1.7 folds higher than that with continuous illumination of white light (0.606 g/L/day). In examples, "continuous illumination" means 24 hours of continuous lighting.

Figure 5:
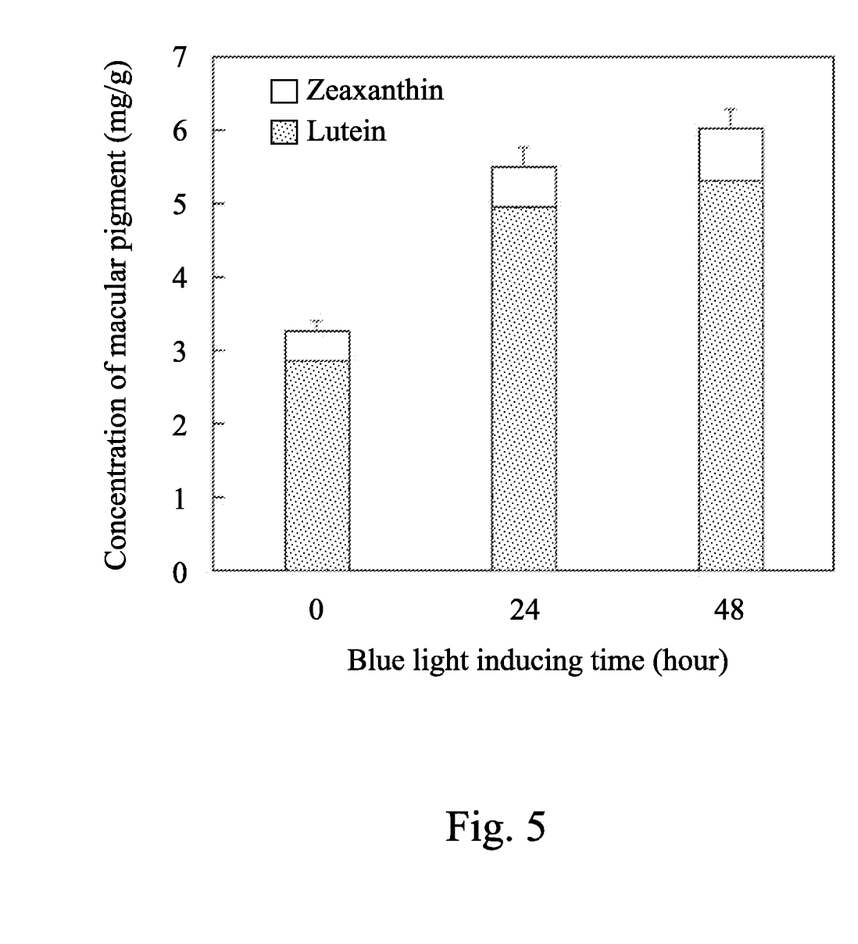
FIG. 5 is a bar chart showing the concentration of macular pigment cultured in pigment inducing unit according to one embodiment of the present disclosure.

The culture device 31 of the pigment inducing unit 30 was a flexible transparent hose, and the length of the flexible transparent hose could be chosen in needed. The flexible transparent hose was bended according to the position of the light source to obtain the maximum lighting area. The culture device 31 (i.e., flexible transparent hose) was made of fluorinated ethylene propylene (FEP) and was 32 millimeters in diameter and 44 meters in length, which could contain 35 L of medium. The second light source 32 was a blue lighting wall comprised of blue LEDs, and the blue lighting wall could emit blue light at both sides of the blue lighting wall. The second light source 32 was surrounded by the culture device 31 twenty-two turns in order to induce the microalgae to produce macular pigment. After the medium containing the microalgae was cultured by the high-density culture unit 20 with the red light, the medium, containing microalgal biomass concentration of 6.5 g/L, flowed to the culture device 31 with 35 L/day flow rate. The medium containing microalgae was continuously illuminated by the blue LEDs (with light intensity of 300 μmol/m$^2$/s) during the retention time of 24 hours and 48 hours (day 13 and day 14). After 24 hours and 48 hours, the amounts of the macular pigment in the microalgae per gram had increased to 5.5 milligrams (mg) per gram (4.9 mg of lutein and 0.6 mg of zeaxanthin) and 6 mg per gram (5.3 mg of lutein and 0.7 mg of zeaxanthin) respectively. Compared with absent of blue light illumination, there were 1.7 folds and 1.8 folds higher. As a result, blue light illumination can induce microalgae to produce macular pigment, and also can produce a large amount of macular pigment in 24 hours, as shown in FIG. 5.

The collecting tank 41 of the harvesting unit 40 had a conical shape. In this example, the collecting tank 41 was a truncated cone, and the diameters of the upper portion and the lower portion were 32 cm and 8 cm respectively, and the truncated cone was 120 cm in height. By using the stirring device 42 located in the bottom of collecting tank 41 and adding flocculant therein, recovery efficiency of the microalgae was enhanced and the recovery time was shortened. The second inlet 411 is located at the upper portion of the collecting tank 41. The three branch pipes 43 are sequentially disposed at a side of the collecting tank 41 and arranged from the upper portion of the collecting tank 41 downward in every 30 cm. The second outlet 412 located at the lower portion of the collecting tank 41 was used for collecting the microalgae, and the branch pipes 43 were used for recovering a supernatant of the microalgae after the flocculation. The supernatant was transported to the outdoor culture unit 10 and used for reutilized.

After the medium containing the microalgae was cultured 24 hours by the pigment inducing unit 30, biomass concentration of *Chlorella* in the medium was 6.5 g/L and the resulting microalgal biomass contained large amount of macular pigment. The medium flowed to the second inlet 411 of the collecting tank 41 at a flow rate of 35 L/day. For the purpose of aggregating the microalgae, a flocculant in food grade, i.e., chitosan, was added into the collecting tank 41 and the mixture was stirred by the stirring device 42. After 24 hours standing, the flocculation efficiency of the microalgae flowing out from each of the branch pipes 43 was measured. The flocculation efficiency of each of the branch pipes 43 from top to bottom were 98% (which means that 98% of the microalgae was remained in the flocculated medium after discharging the supernatants liquid layer from the branch pipe 43 of the collecting tank 41), 95% and 64%. After flocculation, the supernatants in three different layers flowed out from the branch pipes 43 had a total volume of 32 L. The supernatants were collected and transported to the outdoor culture unit 10 for reutilized. 3 L of the microalgal slurry was collected through the second outlet 412 of the collecting tank 41, and the biomass concentration of microalgal slurry was 69 g/L. The supernatant was recovered from the branch pipes 43, thereby reducing waste and saving the cost.

Figure 6:
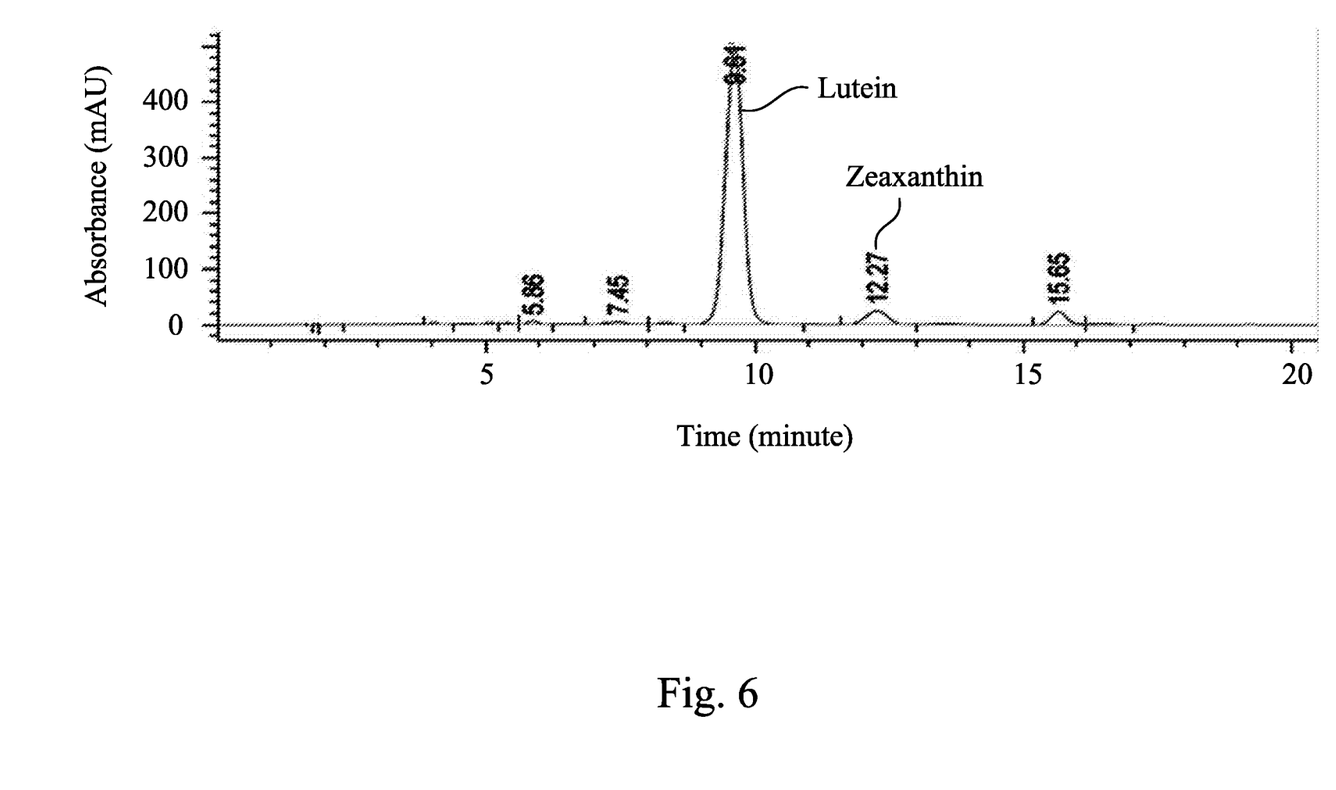
FIG. 6 is a chromatogram showing the high performance liquid chromatography (HPLC) analysis of macular pigment in the microalgae cultured in the pigment inducing unit according to one embodiment of the present disclosure.
Figures 7A, 7B:
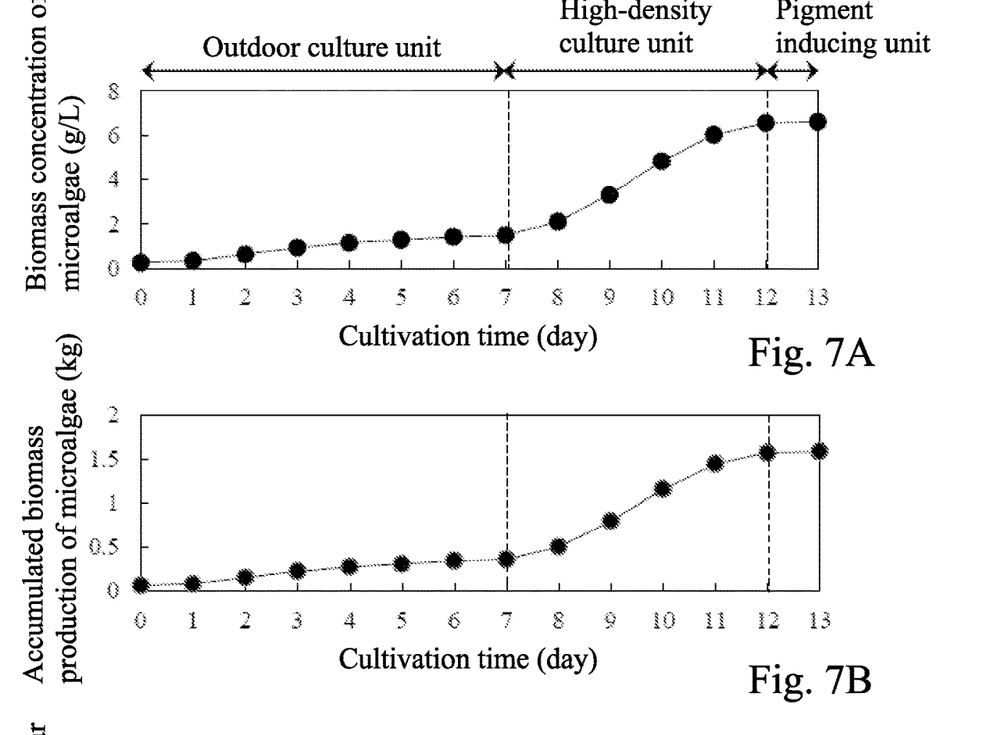
FIG. 7A is a line chart showing the biomass concentration of microalgae.
FIG. 7B is a line chart showing the accumulated biomass production of microalgae.
Figure 7C:
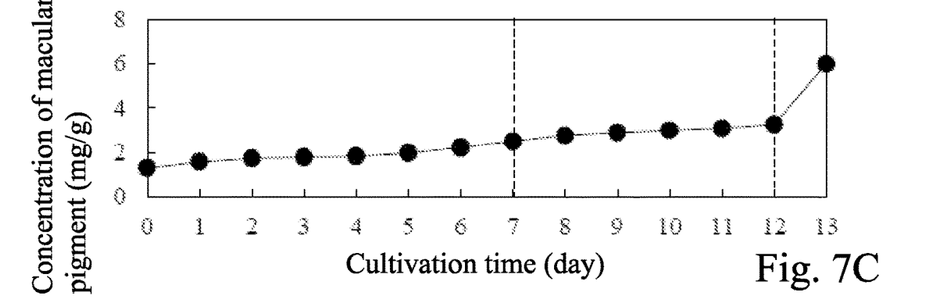
FIG. 7C is a line chart showing the concentration of macular pigment.
Figure 7D:
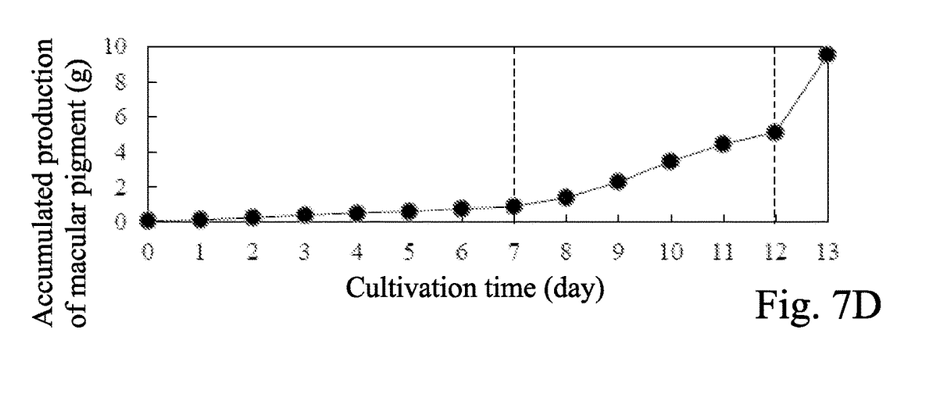
FIG. 7D is a line chart showing the accumulated production of macular pigment.

5 mL of the microalgal slurry containing macular pigment was centrifuged in 3000 g, 10 minutes, and then washed by water. After discarding the supernatant, the microalgal slurry was mixed with 5 mL methanol and extracted for a time period of 30 minutes at 45° C. in a dark environment. The mixture of methanol and microalgal slurry was centrifuged in 3000 g, 10 minutes, and a supernatant methanol containing the macular pigment was collected from the upper layer of the mixture. The supernatant methanol containing the macular pigment was filtered by 0.22 μm polyvinylidene difluoride (PVDF) membrane and analyzed by HPLC. As shown in FIG. 6, the peak areas of lutein and zeaxanthin were obtained at wavelength of 445 nm. After establishing standard curves by using lutein and zeaxanthin standards, the concentrations of lutein and zeaxanthin in the microalgae were 4.8 mg per gram of microalgae (mg/g) and 0.6 mg/g respectively, and the content of macular pigment was 5.4 mg/g. As a result, after the microalgae was induced to produce macular pigment by the blue light, the amount of the macular pigment did not change after the recovery operation and addition of the flocculant in 24 hours.

Exhaust gas discharged from the outdoor culture unit 10 and the high-density culture unit 20 during culture process can be collected by the gas collecting device 61 of the gas recovery unit 60 through the control valves. The recovered exhaust gas was introduced to the first pump 52 and the second pump 53 of the gas supplying unit 50 through the gas controlling device 62. The recovered exhaust gas was mixed with the gas supplied from the gas delivery device 51 to obtain mixed gas, and the mixed gas was introduced into the bottom of each of the first containers 11, 12, 13, 14 and/or the bottom of each of the second containers 21, 22, 23, 24. Therefore, $CO_2$ provided by the gas supplying unit 50 can be absorbed by the microalgae for carbon fixation. The exhaust gas ($CO_2$) not utilized by the microalgae can be collected and recycled by the gas recovery unit 60 thereby reducing waste and saving the cost.

The *Chlorella* was cultured by the continuous microalgae culture module 100 for 13 days, and all data were recorded from day 0 to day 13. As shown in FIG. 7A to 7D, when the *Chlorella* was cultured in the outdoor culture unit 10 for 7 days, the biomass concentration of microalgae was 1.5 g/L and the accumulated biomass production of the microalgae was 0.36 kilograms (kg). When the *Chlorella* was cultured in the high-density culture unit 20 for 5 days from day 7, the biomass concentration of microalgae was significantly increased to 6.5 g/L and the accumulated biomass production of the microalgae was increased to 1.6 kg. The accumulated production of the macular pigment was increased because the accumulated biomass production of the microalgae was increased, but there was no significant increase in the concentration of the macular pigment. In other words, the content of the macular pigment per gram of the microalgal biomass was not significantly increased. When the *Chlorella* was cultured in the pigment inducing unit 30 for 1 day from day 12, the biomass concentration of the microalgae and the accumulated biomass production of the microalgae were not significantly increased. However, the concentration of macular pigment in the microalgae was increased from 3.3 mg/g at day 12 to 6 mg/g at day 13, and the accumulated production of the macular pigment was nearly 10 g.

The continuous microalgae culture module 100, 100" of the present disclosure can produce a large amount of microalgal biomass and macular pigment, by performing operations of connecting each unit in series or in parallel, controlling the flow rate, promoting the growth rate by red light, inducing the macular pigment in the microalgae by blue light, recycling the supernatant medium and effectively collected the resulting microalgal biomass, and continuously operating the module of the present disclosure.

The total culture volume and flow rate can be adjusted in needed, and should not be limited to the description of the embodiments disclosed herein. For example, when the microalgae cultured in the outdoor culture unit 10 and/or the high-density culture unit 20 has reached the maximum growth (close to end of exponential phase) of microalgae, the flow rate and/or medium volume flowing to the next unit can be adjusted.

Although the present invention has been described in considerable detail with reference to certain embodiments thereof, other embodiments are possible. Therefore, the spirit and scope of the appended claims should not be limited to the description of the embodiments contained herein.

What is claimed is:

1. A continuous microalgae culture module, comprising sequentially:
   an outdoor culture unit configured to contain microalgae producing macular pigment and a medium, the outdoor culture unit comprising a plurality of first containers, each one of the first containers comprising:
      a first upper pipe located at an upper portion of each one of the first containers;
      a second upper pipe arranged at a position opposite to the first upper pipe and located at the upper portion of each one of the first containers,
      a first lower pipe located at a lower portion of each one of the first containers, and
      a second lower pipe arranged at a position opposite to the first lower pipe and located at the lower portion of each one of the first containers;
      wherein the first upper pipes and the second upper pipes of the adjacent two of the first containers are connected, and the first lower pipes and the second lower pipes of the adjacent two of the first containers are connected;
   a high-density culture unit connected to the outdoor culture unit, and the high-density culture unit comprising a first light source, the high-density culture unit comprising a plurality of second containers, each one of the second containers comprising:
      a third upper pipe located at an upper portion of each one of the second containers;
      a fourth upper pipe arranged at a position opposite to the third upper pipe and located at the upper portion of each one of the second containers,
      a third lower pipe located at a lower portion of each one of the second containers, and
      a fourth lower pipe arranged at a position opposite to the third lower pipe and located at the lower portion of each one of the second containers;
      wherein the first upper pipe of the first container adjacent to the fourth lower pipe of the second container are connected,
      wherein the first light source of the high-density culture unit is capable of emitting red light;
   a pigment inducing unit, comprising:
      a culture device comprising a first inlet and a first outlet, wherein the first inlet is connected to the third upper pipe of one of the second containers of the high-density culture unit adjacent to the culture device; and
      a second light source adjacent to the culture device, wherein the second light source is capable of emitting a blue light; and
   a harvesting unit, comprising:
      a collecting tank comprising a second inlet and a second outlet, wherein the second inlet is located at an upper portion of the collecting tank and connected to the first outlet of the culture device of the pigment inducing unit, and the second outlet is located at a lower portion of the collecting tank.

2. The continuous microalgae culture module of claim 1, wherein the outdoor culture unit comprises a plurality of first containers, and the first containers are connected in a manner such that the media and the microalgae pass through the first containers in a series or parallel manner.

3. The continuous microalgae culture module of claim 2, wherein the first containers are transparent columns.

4. The continuous microalgae culture module of claim 1, wherein the high-density culture unit further comprises a plurality of second containers, adjacent ones of the second containers are connected with each other, and the first light source is adjacent to the second containers.

5. The continuous microalgae culture module of claim 4, wherein the second containers are connected in a manner such that the media and the microalgae pass through the second containers in a series or parallel manner.

6. The continuous microalgae culture module of claim 4, wherein the second containers are transparent columns.

7. The continuous microalgae culture module of claim 1, wherein the culture device of the pigment inducing unit is a flexible transparent hose surrounding the second light source.

8. The continuous microalgae culture module of claim 1, wherein the harvesting unit further comprises:
   at least one branch pipe located above the second outlet and at one side of the collecting tank, wherein the at least one branch pipe is connected to the outdoor culture unit; and
   a stirring device located inside the collecting tank.

9. The continuous microalgae culture module of claim 1, further comprising:
   a gas supplying unit, comprising:
   a gas delivery device;
   a first pump connected to the gas delivery device and connected to a bottom of the outdoor culture unit; and
   a second pump connected to the gas delivery device and connected to a bottom of the high-density culture unit; and
   a gas recovery unit, comprising:
   a gas collecting device connected to a top of the outdoor culture unit and a top of the high-density culture unit; and
   a gas controlling device connected with the first pump, the second pump of the gas supplying unit and the gas collecting device.

10. A method of culturing microalgae containing macular pigment, comprising sequentially:
   disposing a medium containing microalgae in an outdoor culture unit, and lighting and culturing the medium containing the microalgae at outdoors, such that the microalgae grow to a first density; wherein the outdoor culture unit comprises a plurality of first containers, each one of the first containers comprises:
      a first upper pipe located at an upper portion of each one of the first containers;
      a second upper pipe arranged at a position opposite to the first upper pipe and located at the upper portion of each one of the first containers,
      a first lower pipe located at a lower portion of each one of the first containers, and
      a second lower pipe arranged at a position opposite to the first lower pipe and located at the lower portion of each one of the first containers;
      wherein the first upper pipes and the second upper pipes of the adjacent two of the first containers are connected, and the first lower pipes and the second lower pipes of the adjacent two of the first containers are connected;

after culturing the medium containing the microalgae at outdoors, transporting the medium containing the microalgae to a high-density culture unit, and continuously lighting and culturing the medium containing the microalgae in the high-density culture unit using a red light, such that the microalgae grow to a second density greater than the first density; wherein, the high-density culture unit comprises a plurality of second containers, each one of the second containers comprises:

a third upper pipe located at an upper portion of each one of the second containers;

a fourth upper pipe arranged at a position opposite to the third upper pipe and located at the upper portion of each one of the second containers, a third lower pipe located at a lower portion of each one of the second containers, and a fourth lower pipe arranged at a position opposite to the third lower pipe and located at the lower portion of each one of the second containers;

wherein the first upper pipe of the first container adjacent to the fourth lower pipe of the second container are connected;

after culturing the medium containing the microalgae in the high-density culture unit, transporting the medium containing the microalgae to a pigment inducing unit, and culturing and continuously lighting the medium containing the microalgae in the pigment inducing unit with a blue light, thereby increasing an amount of macular pigment in the microalgae; and after culturing the medium containing the microalgae in the pigment inducing unit, transporting the medium containing the microalgae to a harvesting unit, and collecting the microalgae containing the macular pigment from a bottom of the harvesting unit.

11. The method of claim 10, wherein the medium containing the microalgae is an alkaline medium.

12. The method of claim 10, wherein the microalgae comprise *Chlorella, Nannochloropsis, Dunaliella, Scenedesmus, Chlamydomonas, Spirulina, Botryococcus*, or combination thereof.

13. The method of claim 10, wherein a wavelength of the red light ranges from 600 nm to 700 nm.

14. The method of claim 10, wherein in the step of culturing and continuously lighting the medium containing the microalgae in the pigment inducing unit with the blue light, the blue light has a wavelength ranged from 400 nm to 500 nm.

15. The method of claim 10, wherein carbon dioxide is introduced into the medium containing the microalgae in the outdoor culture unit and in the high-density culture unit simultaneously.

16. The method of claim 10, wherein the step of collecting the microalgae containing the macular pigment from the bottom of the harvesting unit comprises adding a flocculant into and stirring the medium containing the microalgae.

17. The method of claim 16, wherein the flocculant comprises an inorganic flocculant, an organic flocculants, a microbial flocculants, or a combination thereof.

18. The method of claim 17, wherein the flocculant comprises the organic flocculant, and the organic flocculant is chitosan.

19. A continuous microalgae culture module, comprising sequentially:

an outdoor culture unit configured to contain microalgae producing macular pigment and a medium, the outdoor culture unit comprising a plurality of first containers,
wherein a medium containing microalgae is disposed in the outdoor culture unit, and the medium containing the microalgae is lighted and cultured at outdoors, such that the microalgae grow to a first density;

a high-density culture unit connected to the outdoor culture unit, and the high-density culture unit comprising a first light source,
wherein the first light source of the high-density culture unit is capable of emitting red light,
wherein after culturing the medium containing the microalgae at outdoors, the medium containing the microalgae is transported to the high-density culture unit, and the medium containing the microalgae in the high-density culture unit is continuously lighted and cultured by using the red light, such that the microalgae grow to a second density greater than the first density;

a pigment inducing unit, comprising:
a culture device comprising a first inlet and a first outlet, wherein the first inlet is connected to the high-density culture unit; and
a second light source adjacent to the culture device, wherein the second light source is capable of emitting a blue light,
wherein after culturing the medium containing the microalgae in the high-density culture unit, the medium containing the microalgae is transported to a pigment inducing unit, and the medium containing the microalgae in the pigment inducing unit is cultured and continuously lighted with the blue light, thereby increasing an amount of macular pigment in the microalgae; and a harvesting unit, comprising:
a collecting tank comprising a second inlet and a second outlet, wherein the second inlet is located at an upper portion of the collecting tank and connected to the first outlet of the culture device of the pigment inducing unit, and the second outlet is located at a lower portion of the collecting tank,
wherein after culturing the medium containing the microalgae in the pigment inducing unit, the medium containing the microalgae is transported to a harvesting unit, and the microalgae containing the macular pigment are collected from a bottom of the harvesting unit.

* * * * *